United States Patent [19]
Zeibig et al.

[11] 3,979,779
[45] Sept. 14, 1976

[54] CERAMIC IMPLANT
[75] Inventors: Anton Zeibig, Ottensoos; Helmut Locke, Ruckersdorf, both of Germany
[73] Assignee: Rosenthal Technik AG, Selb, Germany
[22] Filed: May 21, 1975
[21] Appl. No.: 579,381

[30] Foreign Application Priority Data
 Nov. 15, 1974 Germany............................ 2454181

[52] U.S. Cl............................................. 3/1.91; 3/1.9;
   3/1.913; 128/92 C; 128/92 CA
[51] Int. Cl.² ........................................... A61F 1/24
[58] Field of Search ............................. 3/1.9–1.913,
   3/1; 128/92 C, 92 CA, 92 B, 92 BA, 92 BB,
   92 BC

[56] References Cited
UNITED STATES PATENTS

| | | | |
|---|---|---|---|
| 2,668,531 | 2/1954 | Haboush | 128/92 CA |
| 3,053,251 | 9/1962 | Black et al. | 128/92 CA |
| 3,314,420 | 4/1967 | Smith et al. | 128/92 C |
| 3,547,115 | 12/1970 | Stevens | 3/1.91 X |
| 3,871,031 | 3/1975 | Boutin | 3/1 |
| 3,894,297 | 7/1975 | Mittelmeier et al. | 3/1 |

FOREIGN PATENTS OR APPLICATIONS
1,334,584  10/1973  United Kingdom............... 128/92 C

*Primary Examiner*—Ronald L. Frinks
*Attorney, Agent, or Firm*—Ostrolenk, Faber, Gerb & Soffen

[57] ABSTRACT

A ceramic implant having at least one component for permanently connecting resected live bone stumps without the use of bone cement or the insertion of an endoprostheses portion into the intramedullar or marrow space of the bone, the implant including at least one cylindrical sleeve having a truncated conical interior recess with rounded grooves helically formed therein for closely engaging a cooperatively formed live bond stump. The ceramic sleeve may be held to the bone stump by use of surgical screws or by a sleeve clamp, to provide a high degree of strength to the resected bone end, as compared to the natural bone strength, immediately after the implanatation operation and to reduce the cortical periphery encased by the implant to promote maximum natural bone growth with minimal inflammation and damage to the marrow space.

16 Claims, 8 Drawing Figures

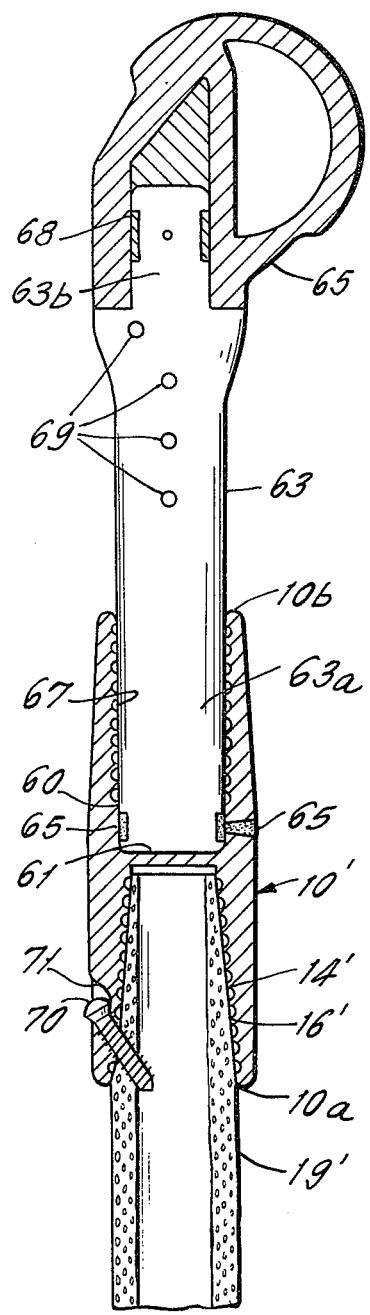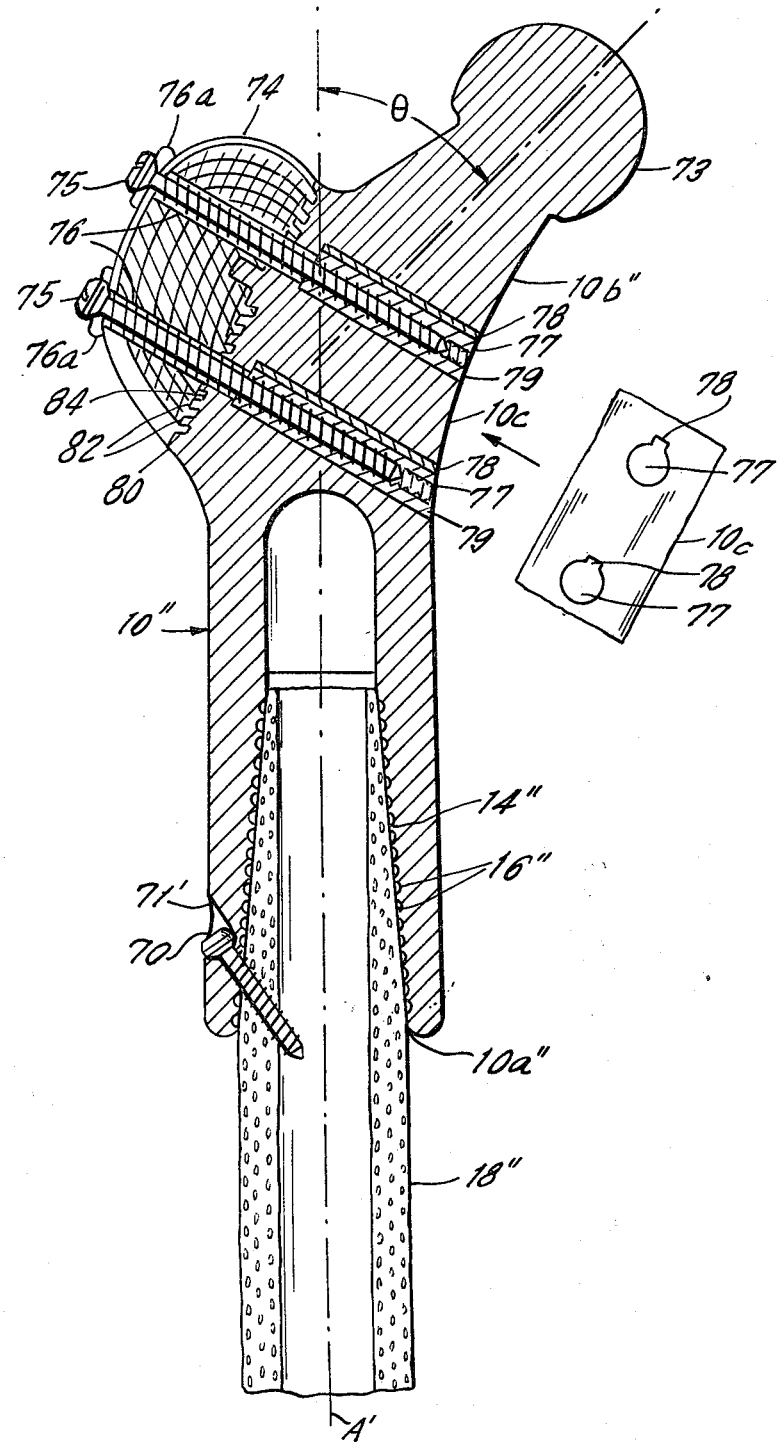

CERAMIC IMPLANT

BACKGROUND OF THE INVENTION

The present invention relates to endoprostheses for joining live bone stubs and more particularly to a novel ceramic implant for bridging over a static defect between live bone ends without requiring the use of bone cement while providing low mechanical stress on the bone surface and encouraging natural bone growth.

It is known to produce implants and endoprostheses of ceramic materials, such as high purity aluminum oxide and the like. Unlike the other conventional implant materials, such as metal compounds or high-polymeric organic plastics and the like, a ceramic material has a permanently stable chemical state, i.e., implants of a ceramic material show no corrosion or disintegration in the living organism due to chemical decomposition by action of body fluids, even after prolonged periods of implantation. High-purity aluminum oxide has the highest degree of tissue compatibility of all the implant materials known at present. It has already been suggested that a multipart hip joint prostheses be provided with a ball and socket formed of aluminum oxide, according to German Patent 1,912,130. A two-part endoprostheses consisting of a metal shaft having a ball of aluminum oxide and a mating socket also of aluminum oxide is described in German published application No. 2,134,316.

The presently known conventional endoprostheses solutions have disadvantages in that they can only be fixed in place by application of bone cement, or as in the above-mentioned German published application 2,134,316, by new natural bone growth, provided the surface of the implant has a porous layer. Both fixing methods have decided disadvantages in that bone cement causes irreversible changes in the adjoining tissue by the exothermic polymerization reaction and by the resulting chemical products, which can lead to inflammation and bond loosening. Additionally, a very large intermedullar free space must be provided for receiving both the prostheses shaft and the bone cement when this technique is used with a tubular bone. This requirement leads to considerable mechanical and biological change along a very great length of the marrow space, due to implant interference with the essential blood supply vessels leading from the marrow space over the spongy resin to the cortical periphery of the bone.

A difficulty encountered in the application of implants having a porous layer is that the strength of the porous surface layer is not sufficient for the mechanical loads subsequently applied thereto. Aggravating the mechanical aspects of intramedullar fixing is the fact that the marrow space has a relatively small diameter, so that considerable force acts on the bone wall over a relatively short shaft diameter having a relatively low bending moment; these forces increase as the shaft of the implant, introduced into the marrow space, becomes shorter.

German patent application P2 305 329.4-35 describes a holding fixture or sleeve designed to prevent splintering or other damage to the bone, but requiring that an intramedullar shaft portion be utilized. The present invention is an additional improvement thereon, which prevents the occurrence of the above-mentioned mechanical and biological problems.

BRIEF SUMMARY OF THE INVENTION

In accordance with the invention, a ceramic implant, useful as a connecting element for a bone or a joint prostheses without using bone cement or requiring entry into the intramedullar or marrow bone spaces, comprises a cylindrical sleeve of ceramic material, such as aluminum oxide, having a truncated conical interior recess formed in one or both axially opposed end surfaces. The interior recess has a thread cut into its interior surface, the thread having a rounded profile and a predetermined pitch and thread depth value, the sleeve having a predetermined cone angle, whereby the thread fits exactly on a machined portion of the bone stump and has an optimal frictional bearing on the living bone.

In one embodiment of the present invention, the female sleeve thread is also cut through to the thread depth by at least one axial longitudinal groove, one groove sidewall having a gradually sloping profile for effecting a tightening fit in the direction of sleeve rotation while the opposite groove sidewall has a suitably steep profile to prevent removal or loosening thereof.

Other embodiments of the present invention include a second truncated conical interior recess opposite the first truncated conical interior recess and having an intermediate bottom member therebetween to join a first bone stump to a second bone stump, using a sleeve clamp, either with or without surgical screws and either with or without a connecting joint spacer placed intermediate the pair of recesses and the bottom members thereof; and an embodiment having a cylindrical recess in the sleeve opposite the truncated conical interior recess, with an intermediate bottom portion therebetween for connection of a living bone stub via a sleeve clamp to a multi-part implant for replacement of a skeletal part, where each ceramic part can be easily adapted to all required skeletal dimensions as only a few variables need be determined; the implant has a plurality of bores provided at various points thereon for connecting sinew- or muscle parts thereto.

The one or more component ceramic implant just described has the advantage that the permanent connection of resected bone ends can be facilitated without the use of bone cement and without intrusion into the intramedullar marrow space while providing a high degree of mechanical strength immediately after the endoprostheses implantation, even while facilitating maximal new bone growth.

Accordingly, it is a primary object of the present invention to provide a one-part or multi-part implant for use as a connecting element in a bone or joint prostheses without using bone cement and without entering the intramedullar marrow space.

It is another object of the present invention to provide such an implant of ceramic material usable with differing skeletal dimensions.

It is a further object of the invention to provide such an implant which provides maximal flexure strength of the repaired bone immediately after prostheses implantation yet does not lead to either an undesireable weakening of the remaining healthy bone or to a decrease of new bone growth.

It is yet another object of the invention to provide such an implant which can be optimally adjusted to frictionally bear upon the living bone stump and which cannot be loosened or counterrotated once emplaced.

It is a still further object of the invention to provide such an implant with means for connecting sinews or muscles at various points thereon.

These and other objects of the invention will become apparent from the following description of the accompanying drawings.

BRIEF DESCRIPTION OF THE DRAWINGS

FIG. 6 is a cross-sectional view of a three-part implant in accordance with the invention for an upper arm bone; and FIG. 7 is a cross-sectional view of a one-part implant for a hip joint and illustrating fastening of the trochanter to the implant.

DETAILED DESCRIPTION OF THE INVENTION

Figure 1:
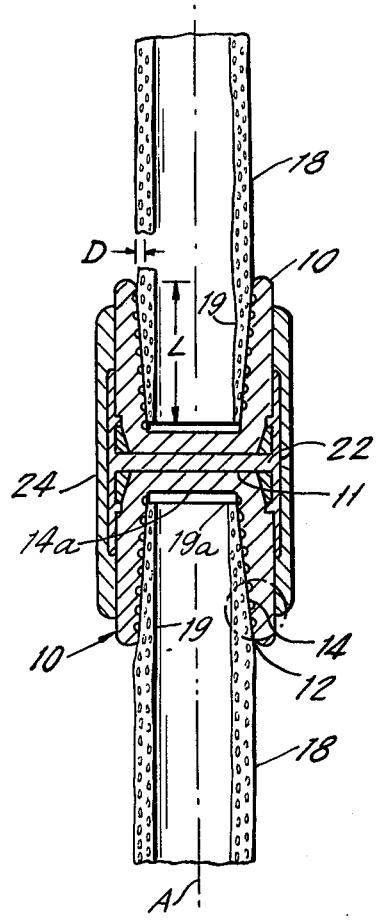
FIG. 1 is a cross-sectional view of a multi-part ceramic implant in accordance with the invention for joining a pair of live bone stumps.
Figure 2:
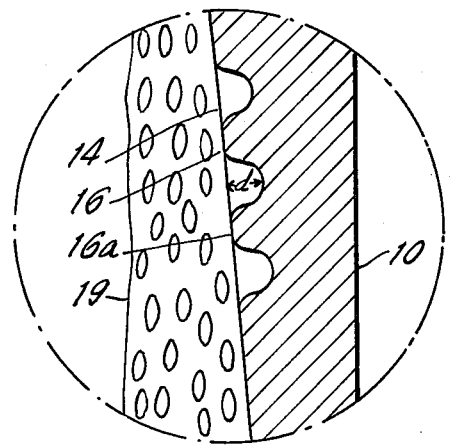
FIG. 2 is an enlarged view of a portion of the ceramic implant of FIG. 1, illustrating the manner in which the implant bears against a prepared bone stump.
Figure 3:
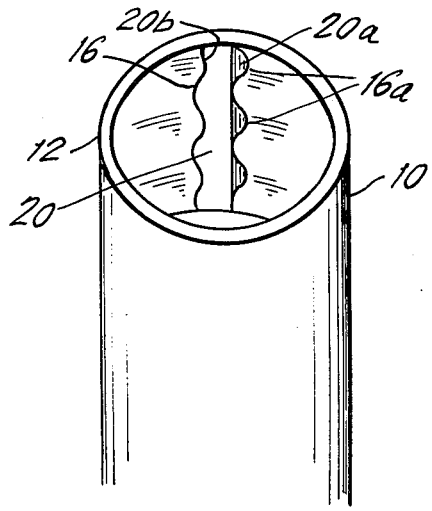
FIG. 3 is a prospective end view of a ceramic implant, in accordance with the invention.

Referring initially to FIGS. 1–3, a generally cylindrical ceramic sleeve 10, preferably fabricated of a high purity aluminum oxide, has a first generally flat end 11 formed substantially transverse to the axis of rotation A of the sleeve. The opposite sleeve end 12 has a truncated conical recess 14 formed therein, having a thread 16 of round or sinusoidal profile formed upon the interior recess surface. Sleeve 10 is designed to closely fit over an end of a live bone stump 18, after the bone stump has been machined with a bevel cutter to have a truncated conical exterior bone portion 19. The original bone dimensions are measured prior to the formation of bone portion 19 and are utilized to establish the cone diameter of sleeve recess 14. Care must be taken when machining the truncated bone portion 19 to achieve a high degree of slimness for thin cortices, against which the innermost thread crests 16a will bear as sleeve 10 is rotated to be frictionally held to bone portion 19.

Thread 16 is characterized in that both pitch and thread depth (d) are, preferably, in a general ratio of 1 plus or minus 20%. To achieve the optimal frictional relationship between the living bone stump 18 and the most inwardly directed thread portions 16a, in the inwardly converging interior recess 14 is characterized by having a cone angle, i.e. a ratio of inward convergence distance (D) to axial length (L), set in the range of 1:10 to 1:6. The female thread 16, in a preferred embodiment, is cut by at least one axial longitudinal groove 20 having a suitably sloping shoulder 20a in the direction of tightening rotation for easily engaging ceramic implant sleeve 10 on formed bone stub 19 and having a suitably steep profile for opposite groove flank 20b to prevent counterrotation and loosening of the implant after attachment to bone stump portion 19.

A suitable sleeve 10 is selected and trimmed to match the cone angle of the machined bone stump 19 and is then rotated by hand onto the machined bone stump until the stump end surface 19a almost touches the inner-most end 14a of the truncated conical recess 14. The space remaining between recess end 14a and bone stump end 19a, as well as the interthread spaces remaining between successive thread crests 16a, allows for new bone growth; the attachment of sleeve 10 to bone stump 18 being enhanced as the new bone growth gradually more completely unites the natural and artificial portions of the resected bone.

FIG. 1 illustrates the use of a multipart ceramic implant to join a pair of resected bone stumps 18. After a ceramic sleeve 10 is frictionally fitted to each machined stump portion 19, the sleeve flat ends 11 are positioned to abut against opposite surfaces of an intermediate bearing member 22 and then secured to each other by means of a sleeve clamp 24 to prevent bone stump separation. Thus, the distance between the pair of resected stump ends 19a is established to maintain the proper skeletal dimensions.

A suitable sleeve 10 is selected and trimmed to match the cone angle of the machined bone stump 19 and is then rotated by hand onto the machined stump until the stump end surface 19a almosts touches the inner-most 14a of truncated conical recess 14. The space remaining between recess end 14a and bone stump end 19a, as well as the interthread spaces remaining between successive thread crests 16a, allows for new bone growth.

After thorough investigation, we have found that an interior sleeve length (L) least 1.5 times the mean diameter ($D_m$) of the machined resected bone end to be introduced, results in an achieved bone strength immediately after the operation which attains an approximate average of 75% of the natural bone strength. We have found that the value of the relative bending force ($F_{rel.}$) of the resected bone-with-sleeve relative to the value of the natural bone flexing strength can be equated to the quotient of length L to mean diameter $D_m$, which quotient is set equal to a variable $h(L/D_m = h)$, as follows:

$$F_{Rel.}(h) = \frac{h}{\sqrt{1 + (\alpha \times h)^2}} \times 100\%$$

Where $\alpha$ is a factor differing only slightly from 1, and hereinafter set equal to one, for reasons of simplicity.

Figure 4:
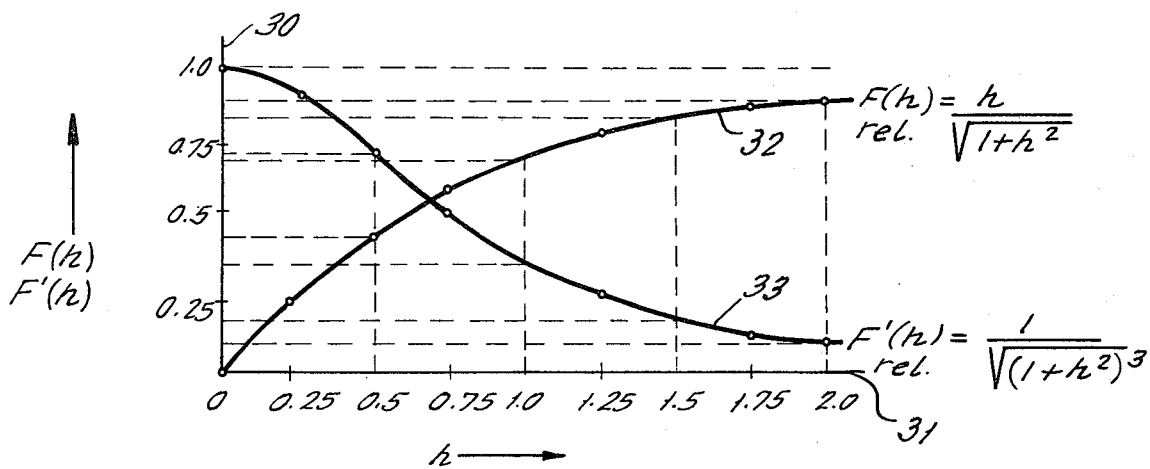
FIG. 4 and 4a are graphs illustrating the relative bone flexure strength derived from the use of a ceramic implant in accordance with the invention.

FIG. 4 shows a graph of this function $F_{rel.}(h)$ and of its first derivative $F_{rel.}'(h)$, both plotted along ordinate 30 for all values of $F_{rel.}(h)$ and $F_{rel.}'(h)$ between 0 and 100% of natural bone flexing strength, and plotted along abscissa 31 for values of length-to-mean-diameter ($h$) between zero and 2.0. The value of flexing force ($F_{rel.}(h)$) sustainable by resected bone stumps 19 with a ceramic sleeve 10 relative to the natural flexing strength values increases, as shown by curve 32, as ($h$) increases; the rate of change $F_{rel.}'(h)$, of this function indicates steeply decreasing gains in relative strength for values of ($h$) in excess of 1.5, as shown by first derivative curve 33. It is desirable to have as short a fixation length L as possible to subject as short a zone of the living bone as possible to biological and mechanical damage caused by implantation of a prosthesis, while still achieving as high a mechanical strength as is possible. Thus, it can be seen that the optimum range for such prosthesis using a ceramic sleeve 10 is found in the interval $1.0 < h < 2.0$. The relative flexing strength can then be selected to achieve any resistance ratio from approximately 70% of the natural bone strength (for a length-to-mean-diameter ration $(h) = 1.0$), to approximately 90% (for $h$ equal to 2.0).

Figure 4A:
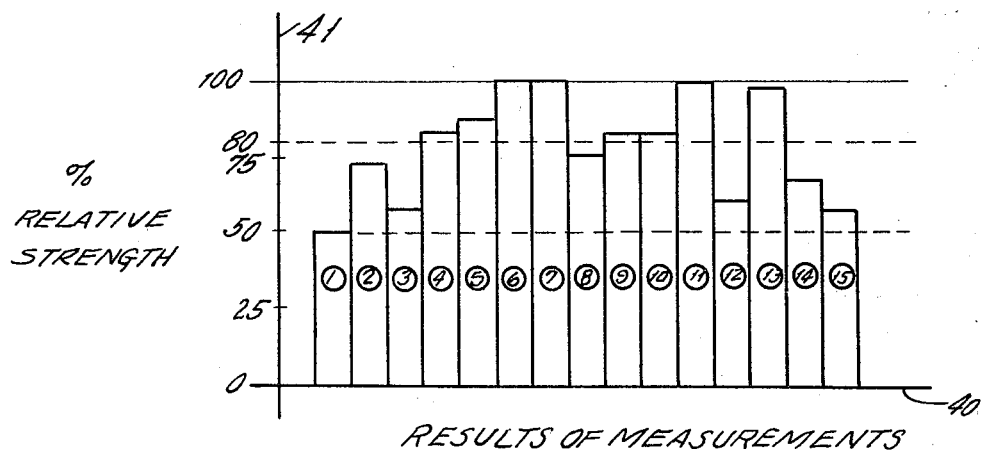

FIG. 4a illustrates the results of a number of strength measurements; the order of experiments is set forth along abscissa 40 and the relative flexing strength between 0 and 100% of the strength of the natural bone is set forth along ordinate 41, for the tapered sleeve of FIG. 1 as used on the upper armbone. From FIG. 4a it can be seen that several of the strength measurements, e.g., measurement 6, 7 and 11, indicate relative flexing strength equivalent to the flexing strength of the humerus without an implant, i.e., having 100% of the natural humerus bone strength; several of the strength measurements, e.g., measurements 1, 3, 12, 14 and 15, have resulted in relative flexing strengths between 50 and 70% of the flexing strength of the natural humerus; and that an average $F_{rel.}$ ($h$) of 80% of the natural strength of the humerus bone is achieved with the implant connection shown in FIG. 1.

Figure 5:
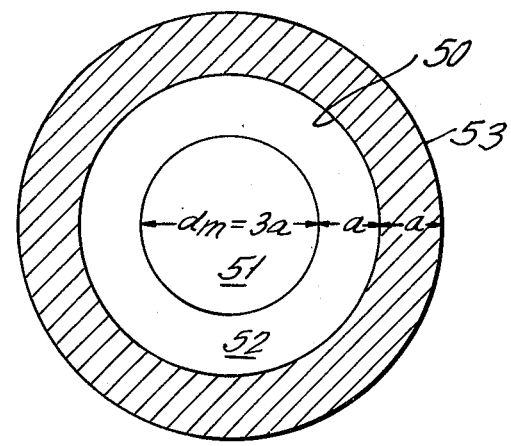
FIG. 5 is a representation of a cross-section of a tubular bone and useful in understanding the present invention.

Referring to FIG. 5, a cross-section of a tubular bone 50 is shown having marrow space 51 and cortical thickness 52 therebetween. Sleeve 53 will cause low specific mechanical stress surface of tubular bone due to the large cross-section of the annular ring-shaped extramedullar fastening, as it will be seen, bu using Wolff's Transformation Law, that a compressive stress can be selected for the bone 50 which not only leads to resorption, but also stimulates new bone growth while permitting a large resistance moment for the implant, relative to the material, in contrast to the previously known intramedullar fixation of the shaft. Thus, with a given permissable material, tension for the attached extramedullar sleeve 10, a substantially higher bending moment can be allowed relative to the bending moment obtainable with the intramedullarly fastened shaft. If, for example, a tubular bone 50 has marrow space 51 of mean diameter $d_m = 3a$, a mean cortical thickness 52 equal to $a$, and a sleeve wall thickness 53 also equal to $a$, the ratio of the resistance moments of sleeve 53 relative to an intramedullarly fastened shaft is 9:1, that is, with equal allowable material tension for both the present invention and the prior intramedullarly fastened shaft, a 9-fold increase amount of the bending moment can be transmitted with sleeve 53 relative to the intramedullarly fastened shaft.

Referring now to FIG. 6, a second embodiment of ceramic implant sleeve 10' includes a first end 10a having an axially aligned truncated conical interior recess 14' formed therein and an opposite end 10b having an axially aligned cylindrical recess 60 formed therein, with an intermediate bottom portion 61 formed between the most inwardly directed ends of conical recess 14' and cylindrical recess 60. Cylindrical recess 60 is adapted to receive a cylindrical end 63a of a spacer 63 having a length selected to join the trimmed bone stub 19 to a ball section 65 having a diameter selected for proper mating with a bone socket (not shown). Spacer 63, representing an upper arm bone in this example, is molded preferably of polymethyl methyacrylate and is adapted to closely fit into cylindrical sleeve recess 60. Cylindrical recess 60 and the spacer cylindrical end 63a are both provided with coordinated ring slots 65 for receiving polymethyl methacrylate to form a bond of sufficient strength therebetween, as may be further aided by the application of polymethyl methacrylate within the threads 67 formed on the interior surface of cylindrical recess 60. Ground ball end 65 is partly hollow and is attached on a shaft journal portion 63b which contains a set of grooves 68 to prevent rotation under stress of ball 65 about shaft journal portion 63b. Ceramic ball end 65 and shaft journal portion 63b are joined to each other by injecting polymethyl methacrylate within grooves 68. The multi-part implant of ceramic ball 65, shaft 63 and ceramic sleeve 10' is placed into the socket, not shown, of the shoulder joint and the overlying sinews and muscle parts are connected at certain points as provided by a plurality of bores 69 formed through an intermediate portion of shaft 63, until all overlying sinews, muscles and derma are sewn up layer by layer to complete the implant operation. An orthopedic screw 70 may be introduced through a pre-formed bore 71 in the wall of the truncated conical recess portion 14', as may be required to to further prevent implant rotation relative to the lower arm bone 19', until new bone growth fills the space between threads 16' to tightly hold the implant in place.

FIG. 7 illustrates a hip joint endoprosthesis, a one-piece ceramic implant 10'' having a truncated conical recess 14'' formed in a first end 10a'', and having threads 16'' formed upon its interior surface. The opposite end 10b'' of the ceramic implant has a ceramic ball portion 73 of a size, shape and offset angle $\theta$ relative to the extension of the axis A' of bone 18'', as required for the particular patient. A particular feature of this embodiment of the ceramic implant is that the trochanter part 74 is secured directly upon the implant by surgical screws 75. A first set of bores 76 having a diameter calculated to allow close passage of each screw 75 therethrough are formed through trochanter part 74. A second set of bores 77 are cooperatively formed through an intermediate section 10c of the ceramic implant in axial alignment with trochanter part bores 76. Each ceramic implant bore 77 has a generally larger diameter than trochanter bore 76 and includes an axial aligned and generally rectangularly shaped groove 78 formed further into ceramic implant intermediate portion 10c along a portion of the interior surface of each bore 77 to prevent rotation of plastic casting material 79 which is molded into each bore 77 to engage the associated screw 75. A screw 75 is placed through first bore 76 and into second bore 77; plastic casting material 79, such as polymethyl methylcrylate, is injected into the remaining open bore space 77, 78. After polymerization of the casting material, each screw 75 can be withdrawn; the resulting plastic thread formed in casting material 79 is now specifically adapted to the threaded profile of a particular screw 75 so that each screw can only be rotatably engaged against a certain resistance. Thus, each portion of plastic material 79 serves not only as a rotation-lock in cooperation with groove 78, but also serves as a lock nut cooperating to prevent the withdrawal of the engaged screw 75. Each screw 75 rests firmly in a seat portion 76a formed within the plastic portions 76 for any screw position even under stress.

It has also been found expedient to provide ceramic implant 10'' with a trochanter seat surface 80 having a plurality of grooves 82 cut therein at a small angle to the surface normal line for receiving tongues 84 of newly formed bone substance. The interlocked pluralities of implant grooves 82 and tongues 84 of new bone growth enhance the rate of new bone growth, as can be demonstrated by provisional cystological tests, yet prevent a detachment of the natural bone parts.

The advantages achieved with the present invention particularly include an implant which is no longer required to be inserted into the bone marrow space or cemented by bone cement. The ceramic sleeve serves as a supporting and connecting element and does not function, as the known implants do function, to prevent splintering of the enclosed bone due to the stress of the inserted surgical screw. Maximal force transmission is realized due to the exact fit between the tapered implant sleeve and the coordinately tapered bone stump, whereby a force acts upon the entire conical bone stump even though the latter has a weakened end due to the trimming of the bone stump. During the machining of the bone stump so called "asymptotic" tongues are formed at the conical surface end because of the bone stump irregular cross-section; the asymptotic tongues are particularly suitable to enhance the formation of new bone substances between the bone stump and the implant. The most important advantage, however, has proved to be the preservation of the bone marrow, so that the extremely important blood supply paths for new bone growth are maintained to a greater extent than here to before possible.

There has just been described a novel one-or multipart ceramic implant for the permanent connection of resected bone ends or the formation of skeletal joints without intrusion into the intramedullar marrow space and without the use of bone cement, yet providing a high degree of mechanical strength immediately after the endoprosthesis implantation and facilitating maximal new bone growth.

While several preferred embodiments of this novel invention have been described, many variations and modifications will now become apparent to those skilled in the art. Therefore, this invention is to be limited, not by the specific disclosure herein, but only by the appended claims.

What is claimed is:

1. An implant for forming a permanent connection to a bone stump having a cortical periphery resected to have a generally truncated conical exterior surface, said implant comprising:
   a ceramic sleeve of generally cylindrical shape having first and second end surfaces;
   said sleeve having a recess converging into said first end surface, said recess having a generally truncated conical interior surface adapted to frictionally engage said resected bone stump cortical periphery; and
   means formed on said recess interior surface for further frictionally engaging said cortical periphery, whereby new bone growth on said bone stump is enhanced to further join said sleeve to said bone stump.

2. An implant as set forth in claim 1, wherein said first means includes a screw thread formed in said recess interior surface, the crest portion of said screw thread forming said recess interior surface, and the trough portion thereof outwardly extending into said sleeve to form a volume to be filled by said new bone growth.

3. An implant as set forth in claim 2, wherein the screw thread has a generally sinusoidal profile.

4. An implant as set forth in claim 2, wherein a ratio of the pitch of the screw thread to the depth of said trough into said recess inerior surface is equal to 1 ± 20%.

5. An implant as set forth in claim 2, wherein the screw thread is cut by at least one axial groove formed in the recess interior surface.

6. An implant as set forth in claim 5, wherein a first flank of said groove has a gradually rising profile in a first radial direction and an opposite flank of said groove has a generally steeply rising profile in an opposite radial direction, whereby said gradual profile allows said sleeve may be tightened by rotation in said first direction and said steeply profiled flank prevents said sleeve from being loosened by rotation in said opposite direction.

7. An implant as set forth in claim 6, further including another truncated conical recess converging into said second end surface, said second truncated conical recess having an interior surface adapted to cooperatively frictionally engage a cortical periphery of another resected bone stump.

8. An implant as set forth in claim 7, wherein said sleeve has a bottom portion intermediate said first and said second conical recesses, whereby an end surface of said first resected bone stump is spaced a predetermined distance from an end surface of said another resected bone stump when said implant is fastened therebetween.

9. An implant as set forth in claim 1, wherein said truncated converging conical recess is formed in said first end surface to a predetermined depth, said recess having a first predetermined diameter at said first end surface and having a second predetermined diameter at said predetermined distance inward from said first end surface;
   said recess having a cone angle defined as the ratio between said predetermined depth and the difference between said first and second recess diameters;
   said cone angle being in the range of about 6:1 to 10:1.

10. An implant as set forth in claim 9, wherein a ratio of said recess depth to a mean value of said first and second recess diameters is selectable over a range from said ratio equal to 1 to said ratio equal to 2.

11. An implant as set forth in claim 1, wherein said sleeve further includes a generally cylindrical recess formed in said second end surface, said cylindrical recess and said sleeve having generally parallel aligned axes of rotation.

12. In combination, the implant of claim 11 and a skeletal spacer member having a generally cylindrical first end; said sleeve cylindrical recess having an interior diameter adapted to frictionally engage said spacer member first end in axial alignment therein.

13. A combination as set forth in claim 12, wherein said spacer member first end further includes at least one inwardly directed formation in an exterior surface thereof; an interior surface of said sleeve cylindrical recess further includes a cooperatively inwardly directed formation alignable with each of said spacer member surface formations when said spacer member first end is completely seated within said sleeve cylindrical recess; and a bonding material introduced in said cooperating recess and spacer surface formations, whereby a bond of sufficient strength to prevent rotation of said spacer member with respect to said sleeve is established.

14. A combination as set forth in claim 12, further including joint ball means coupled to another end of said spacer member.

15. A combination as set forth in claim 12, wherein an intermediate portion of said spacer member includes at least one aperture; and further including surgical fastening means entered into each said intermediate portion aperture for securing another bone part to said intermediate spacer member portion; and a bonding material injected into each said intermediate portion aperture for engaging an end portion of each said surgical fastening means, whereby said fastening means is prevented from being loosened from said intermediate portion aperture under stress.

16. An implant as set forth in claim 1, further including an aperture entered into the exterior cylindrical surface of said sleeve and communicating with said truncated conical recess; and surgical fastening means positioned through said aperture for additionally securing said sleeve to said bone stump positioned in said sleeve recess.

* * * * *